(12) United States Patent
Marra

(10) Patent No.: US 7,857,892 B2
(45) Date of Patent: Dec. 28, 2010

(54) AIR POLLUTION SENSOR SYSTEM

(75) Inventor: Johan Marra, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 516 days.

(21) Appl. No.: 11/573,293

(22) PCT Filed: Aug. 10, 2005

(86) PCT No.: PCT/IB2005/052651

§ 371 (c)(1),
(2), (4) Date: Feb. 6, 2007

(87) PCT Pub. No.: WO2006/016346

PCT Pub. Date: Feb. 16, 2006

(65) Prior Publication Data

US 2008/0041138 A1     Feb. 21, 2008

(30) Foreign Application Priority Data

Aug. 11, 2004  (EP) .................. 04300526
Jan. 14, 2005  (EP) .................. 05300034
Jun. 28, 2005  (EP) .................. 05105741

(51) Int. Cl.
*B03C 3/68*     (2006.01)
(52) U.S. Cl. .................. 96/19; 95/3; 96/16; 96/67; 96/77; 96/96; 96/97
(58) Field of Classification Search .................. 96/19, 96/67, 68, 77–79, 96, 97, 111, 399, 417, 96/16; 95/3
See application file for complete search history.

(56) References Cited

U.S. PATENT DOCUMENTS

| | | | |
|---|---|---|---|
| 4,574,004 A | | 3/1986 | Schmidt-Ott et al. |
| 4,837,440 A | | 6/1989 | Burtscher et al. |
| 5,035,728 A | * | 7/1991 | Fang .................. 96/19 |
| 5,403,383 A | * | 4/1995 | Jaisinghani .......... 95/69 |
| 5,431,714 A | | 7/1995 | Burtscher et al. |
| 5,725,425 A | | 3/1998 | Rump et al. |

(Continued)

FOREIGN PATENT DOCUMENTS

DE          19824744 A1     3/1999

(Continued)

OTHER PUBLICATIONS

Written Opinion of the International Searching Authority PCT/IB2005/052651, Jan. 12, 2005.

*Primary Examiner*—Richard L Chiesa

(57) ABSTRACT

The disclosure relates to an air pollution sensor system incorporated in an enclosure, the enclosure including an air handling system inside an air duct, the air duct enabling a communication between air inside the enclosure and air outside the enclosure. The air duct including an air inlet for receiving air and an air outlet for releasing handled air inside the enclosure. The air pollution sensor system includes at least one ultra fine particle sensor capable of sensing particles with a diameter in a range of approximately 5-2500 nm, preferably in a range of approximately 5-1000 nm and more preferably in a range of approximately 5-500 nm inside the enclosure and providing a pollution information signal in response to the sensing of the particles. The disclosure further relates to various types of ultra fine particle sensors and air handling systems.

19 Claims, 13 Drawing Sheets

U.S. PATENT DOCUMENTS

| | | |
|---|---|---|
| 5,775,415 A | 7/1998 | Yoshimi et al. |
| 5,980,614 A * | 11/1999 | Loreth et al. ............... 96/63 |
| 6,623,544 B1 * | 9/2003 | Kaura ........................ 95/3 |
| 7,235,120 B2 * | 6/2007 | Dennis ....................... 95/2 |
| 2001/0032544 A1 * | 10/2001 | Taylor et al. .............. 96/19 |
| 2003/0165410 A1 | 9/2003 | Taylor |
| 2004/0074387 A1 * | 4/2004 | Jaisinghani ................ 95/63 |
| 2004/0141875 A1 | 7/2004 | Doshi |

FOREIGN PATENT DOCUMENTS

| | | | |
|---|---|---|---|
| DE | 10255152 A1 | 6/2004 | |
| EP | 0457224 A1 | 11/1991 | |
| FR | 2838379 A1 | 10/2003 | |
| JP | 6-126212 A * | 5/1994 | ............... 96/19 |

* cited by examiner

AIR POLLUTION SENSOR SYSTEM

This case is the national stage of International Application No. PCT/IB05/52651, filed on Aug. 10, 2005.

FIELD OF THE INVENTION

The invention relates to an air pollution sensor system. The invention further relates to a sensor unit and an air handling system installable in such an air pollution sensor system.

BACKGROUND OF THE INVENTION

During the past ten years, it has become increasingly clear that the inhalation of airborne combustion-related ultra fine particles (UFPs) presents a significant health-hazard to humans, owing to the fact that these particles tend to deposit on and eventually encapsulate in the lung tissue. Such UFPs comprise both solid particles and liquid-like particles. A significant part of the combustion-related solid particles is composed of soot particles that comprise or largely consist of unburned elemental carbon. A smaller part of the combustion-related solid particles is composed of inorganic ashes. Ultra fine combustion-related liquid-like particles are typically composed of more-or-less volatile hydrocarbon/$H_2SO_4$/$H_2O$ material together with small amounts of inorganic species. Combustion-related UFPs measure approximately between 5 and 2500 nm in diameter, in particular between 5 nm and 500 nm in diameter (most particles measuring less than 200-300 nm in diameter), and normally comprise or are at least partially covered with carcinogenic polycyclic aromatic hydrocarbons (PAHs) and other volatile organic compounds (VOCs). These UFPs are emitted into air from the exhaust of combustion sources such as automobile motors and are formed as the result of an incomplete combustion process. In particular diesel motors are notorious for emitting large amounts of soot particles and other UFPs into air.

Apart from the neighborhood of industrial combustion sources and other stationary combustion sources, the concentration of combustion-related UFPs, hereafter simply referred to as UFPs, in the western world is generally highest on or near locations where motorized traffic is present. Very high local concentrations may be encountered particularly in tunnels, traffic intersections and/or in traffic queues under conditions of limited ventilation and/or windspeed. However also in (rooms of) buildings, recreational cabins, huts, homes, vessels, aircraft, spacecraft, and individual compartments/rooms inside said vehicle cabins, recreational cabins, huts, homes, buildings, vessels, aircraft, and spacecraft, highly health-hazardous concentrations of UFPs may be encountered.

Especially automobile drivers and passengers become readily exposed to elevated concentrations of UFPs and other exhaust pollutants because the vehicle's air handling system (which may e.g. be either a heating, ventilating, air conditioning (HVAC) system or a basic heating/ventilation system) continuously draws outside air, that is polluted by the exhaust gases and particles emitted from the exhausts of other vehicles, into the vehicle cabin. It is therefore desirable to be able to at least partly clean the outside air of various airborne pollutants by means of an air cleaning unit before allowing its entrance into the cabin, and to automatically control the settings of the air handling system in response to conditions pertaining to the outside air, notably the humidity, the temperature and the pollution level, in order to minimize the exposure of the vehicle's inhabitants to air pollutants, while retaining comfortable temperature and humidity levels.

As described in U.S. Pat. No. 5,775,415, the operation mode of the vehicle's air handling system can be controlled by an electrical control unit that actuates and controls the rotation of a switching damper element, positioned between the cabin air inlet and the outside air inlet associated with the air handling system. The switching damper element is rotated such as to fully close the cabin air inlet and to fully open the outside air inlet in the input mode operation, while fully opening the cabin air inlet and fully closing the outside air inlet in the re-circulation mode operation. In the mixed mode operation, the switching damper element can assume a series of intermediate positions that partly open both the cabin air inlet and the outside air inlet such that a controlled amount of re-circulating cabin air and a controlled amount of outside air are simultaneously allowed to enter the air handling system.

SUMMARY OF THE INVENTION

It is an object of the invention to provide an air pollution sensor system for an enclosure containing an air handling system, wherein said air pollution sensor system is apt to provide information on the pollution of the air within said enclosure with respect to ultra fine particles.

To this end, an air pollution sensor system is provided.

The application of an ultra fine particle (UFP) sensor in the air pollution sensor system generates specific information on the pollution by UFPs within the enclosure. Since the inhalation of airborne UFPs is known to be far more hazardous to human health than the inhalation of common exhaust gases, it is important to recognize the airborne UFP concentration as an important contributor to the air pollution level. In this regard, the air pollution sensor system comprises an UFP sensor while the air handling system may have characteristics that make it particularly suitable for the removal of UFPs from air prior to its release inside the enclosure.

An embodiment of the invention provides the advantage that the performance of the air cleaning unit with respect to UFPs can be evaluated. The difference between e.g. the air pollution level inside the enclosure and the outside air pollution level is often directly determined by the efficiency of an air cleaning unit of an air handling system, at least in case no pollution sources are present within the enclosure.

Another embodiment of the invention provides the advantage that the contribution of pollution sources of UFPs not entering the enclosure via the air duct can be taken into account. Examples include the presence of pollution sources inside the enclosure, such as inhabitants smoking a cigarette, or UFPs entering the enclosure via an open window.

Another embodiment of the invention provides the advantage that both the concentration of UFPs entering the enclosure via the air duct and the concentration of UFPs present within the enclosure away from the air duct can be detected independently from each other, and information can be provided with respect to both the UFP concentration in the air entering the enclosure via the air duct and the UFP concentration in the air inside the enclosure away from the air duct that is actually inhaled by people residing in the enclosure. This embodiment is particularly useful to unambiguously detect the presence of air pollution sources inside the enclosure.

Another embodiment of the invention provides the advantage of enabling an automatic variation in the operation of the air cleaning unit as a function of the sensed UFPs, e.g. the concentration(s) of UFPs. If the pollution level within the enclosure and/or downstream of said air cleaning unit increases e.g. above a certain threshold, the pollution information signal may control the air cleaning unit to improve its cleaning operation with respect to UFPs such that the UFP concentration in the air inhaled by people inside the enclosure returns to an acceptable value.

Another embodiment of the invention provides the advantage of controlling the air flow through the air duct. The air cleaning efficiency may depend on the amount of air that is displaced by the air handling system per unit of time because this determines the air speed through the air cleaning unit.

Another embodiment of the invention provides the advantage that charging of airborne UFPs has been found to be an effective means for allowing the accomplishment of a significant increase in the UFP filtration efficiency of a filtering section that is positioned downstream of the UFP charging section.

It is a further object of the invention to provide a sensor unit for adequately sensing UFPs.

To this end, a sensor unit is provided.

It has been found that the occurrence of a net electrical charge on airborne UFPs allows an adequate and reliable sensing of these airborne UFPs.

Another embodiment of the invention provides the advantage that most if not all UFPs become charged before entering the precipitation section. This may e.g. be desirable in case of insufficient charging of UFPs by an upstream air cleaning unit or in the complete absence of any upstream charging section.

Other embodiment (s) of the invention comprise an effective means for sensing the charged UFPs by application of an electric field between electrodes, preferably parallel-plate electrodes. Parallel plates have the advantage of incurring only a negligible air pressure drop within e.g. the air duct of the enclosure.

Another embodiment of the invention comprises another suitable means for sensing UFPs. The advantage of using a fibrous dust filter inside a Faraday cage (that is connected via a sensitive current meter to earth potential) for capturing charged UFPs from the air passing though the UFP sensor unit lies in the circumstance that no voltage differences need to be applied to the precipitation section which avoids the existence or voltage-induced capacitive currents, thus making the accurate measurement of small electric currents arising from the deposition of charged airborne particles inside the Faraday cage associated with the precipitation section much easier to accomplish.

It should be acknowledged that the embodiments described above, or aspects thereof, may be combined.

It is a still further object of the invention to provide an air handling unit capable of removing airborne UFPs from an air flow.

To this end, an air handling system is provided.

It has been found that a charging of UFPs provides for a very effective means for facilitating and improving the removal of at least a part of the UFPs from an air flow.

Another embodiment of the invention provides the advantage of an effective means for charging UFPs, in particular soot particles, in order to remove these UFPs in the filtering section. Another embodiment of the invention is effective in charging different types of UFPs.

Another embodiment of the invention provides the advantage that ozone gas, generated from e.g. a quartz ultraviolet lamp, is prevented from leaving the sensor unit.

Other embodiments of the invention provide filtering sections capable of effectively removing UFPs from air.

It should be acknowledged that the embodiments described above, or aspects thereof, may be combined.

The invention will be further illustrated with reference to the attached drawings, which schematically show preferred embodiments according to the invention. It will be understood that the invention is not in any way restricted to these specific and preferred embodiments.

DETAILED DESCRIPTION OF THE DRAWINGS

Figure 1:
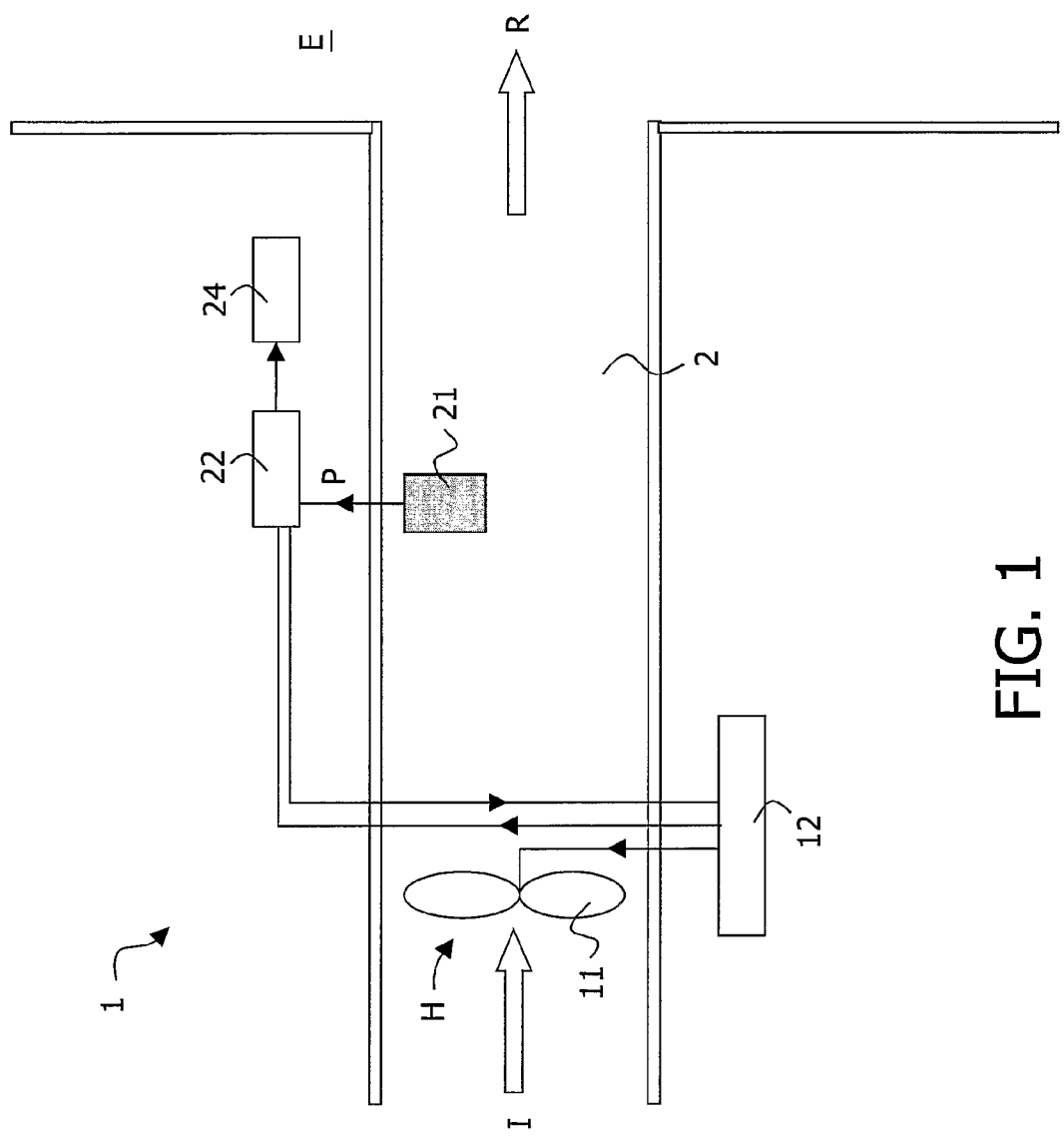
FIGS. 1-5 show schematic diagrams of an air pollution sensor system in an enclosure comprising an air handling system inside an air duct, according to embodiments of the invention.

The present invention discloses an air pollution sensor system 1, shown in FIGS. 1-5, incorporated in an enclosure E. The enclosure E comprises an air handling system H inside an air duct 2, said air duct 2 enabling a communication between air inside said enclosure E and air outside said enclosure E. The air duct 2 comprises an air inlet for receiving air I and an air outlet for releasing handled air R inside said enclosure E.

The enclosure E may be any kind of residence/dwelling, including vehicle cabins, recreational cabins, huts, homes, buildings, vessels, aircraft, spacecraft, and individual compartments or rooms inside said vehicle cabins, recreational cabins, huts, homes, buildings, vessels, aircraft and spacecraft. Hereinafter only the specific example of a vehicle cabin enclosure will be described in more detail but it should be noted that an entirely analogous description applies to all other mentioned enclosures. Furthermore, it should be noted that the air handling system H may or may not comprise heating and/or cooling means. A mentioning of the air handling system being embodied as a HVAC system (thus formally comprising heating and cooling means) does not exclude the air handling system to be embodied as an ordinary air handling system without heating and/or cooling means. The term "HVAC" does not imply a requirement for the presence of means for air heating and/or air cooling.

The air handling system H may e.g. comprise a HVAC ventilator 11 for displacing air through said air duct 2 and/or an air cleaning unit 13 for cleaning air passing said air cleaning unit 13. The air pollution sensor system may comprise control electronics including e.g. an HVAC controller unit 12 and an air cleaning controller unit 14. The HVAC controller unit 12 tunes the ventilation speed and selects the mode of HVAC operation comprising normal inlet-mode operation, re-circulation mode operation or mixed-mode operation.

At least one ultra fine particle sensor 21 is provided capable of sensing particles with a diameter in a range of approximately 5-2500 nm, preferably approximately 5-1000 nm and more preferably in a range of approximately 5-500 nm, hereinafter to be referred to as ultra fine particles (UFPs). Upon sensing UFPs, the sensor 21 provides a pollution information signal P.

Evaluation of output signals from the air cleaning unit 13 and/or the sensor 21 is respectively performed by an air cleaning evaluation unit 23 and an air pollution evaluation unit 22. An air pollution indication unit 24 is present to provide pollution information to inhabitants of the enclosure E.

FIG. 1 shows an embodiment comprising a single sensor 21 without an air cleaning unit inside a vehicle's HVAC system. A coarse pre-filter (not shown) upstream of the ventilator 11 may be present to remove large debris from air. The particle air pollution information signal P obtained from the sensor 21 is evaluated by an air pollution evaluation unit 22 and visualized on an air pollution indicator/warning unit 24.

In inlet mode operation, only the particle pollution in the outside air is recorded and it is this pollution that also enters the vehicle cabin E. During normal inlet mode operation, it is not possible to detect smoking activities or a presence of open cabin windows (it is of course possible to detect open windows electronically). In case the measured particle pollution level entering the cabin exceeds a given threshold, the air pollution evaluation unit 22 will trigger the HVAC controller 12 to switch from normal inlet mode operation to re-circulation mode operation in order to avoid continued passage of large amounts of pollutants into the cabin E. Re-circulation gradually leads to a reduction of the UFP concentration because of particle deposition on the various walls inside the air duct 2 and the cabin interior E. Re-circulation will only continue for a limited period of time (in order to keep the carbon dioxide and/or moisture concentration inside the cabin within safe and comfortable limits) after which outside air I is again allowed to pass into the vehicle cabin E for at least a minimum period of time by switching the air handling system H back to inlet mode operation. Thereafter the air handling system may again be switched into re-circulation mode operation in case the outside air pollution is still too high.

In case of normal inlet-mode operation, it is not possible to detect smoking or intrusion of pollutants through open windows in the embodiment of FIG. 1. Of course, a presence of open windows can be electronically detected and such information may always be relayed as a warning to the vehicle inhabitants, in particular when the outside air pollution has become sufficiently high to have triggered a change from inlet-mode operation to re-circulation mode operation. In case of re-circulation mode operation and closed windows, smoking activity is detected when the recorded particle pollution increases in the course of time because cabin air re-circulation brings the smoke particles in contact with the sensor 21. This may then be indicated as a warning signal on the air pollution indicator/warning unit 24 to the vehicle inhabitants that smoking has been detected and that the encountered air pollution endangers human health. At the same time, detection of smoking triggers a return to inlet-mode operation while increasing the ventilation speed through the cabin, for at least a minimum set period of time, in order to remove the smoke particles from the cabin E as quickly as possible. After that period of time, it is sensed whether the sensed particle pollution level (in the outdoor air) is still at such a high level as to trigger again at least a temporary switch to re-circulation-mode operation and the described sequence of events may be repeated. In the embodiment of FIG. 1, only a limited degree of personal protection against exposure to particle pollutants from the outside air is accomplished.

Figure 2:
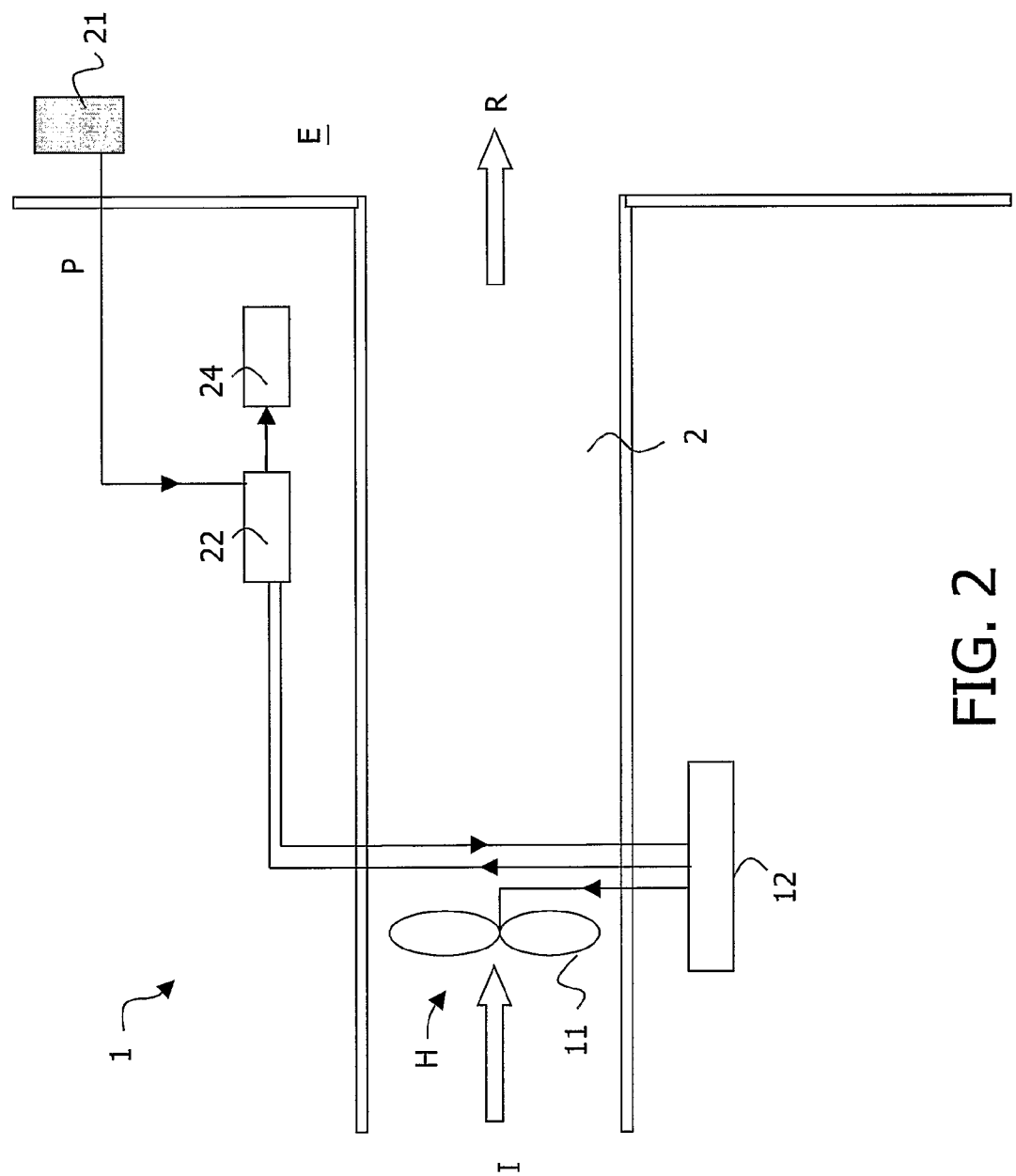

FIG. 2 shows an embodiment with the particle sensor 21 in the cabin E instead of in the air duct 2. No air cleaning unit is present. In contrast with the embodiment of FIG. 1, the pollution level of UFPs is now directly sensed in the air of the cabin E, which air is inhaled by the inhabitants. During normal inlet mode operation, it is not possible to detect the presence of UFPs that are specifically introduced from smoking and/or open windows, only the actual particle pollution level in the cabin E and this may be made visible on an air pollution indicator unit 24. In case the recorded particle pollution exceeds a set threshold pollution level, a trigger signal is send to the controller unit 12 to switch to re-circulation mode operation for at the most a set maximum period of time.

In case of closed windows and absence of smoking, this measure will slowly decrease the recorded particle pollution level. When the recorded pollution level has fallen below a second set pollution level, the system is switched back to normal inlet mode operation. Alternatively, a switch back to inlet mode operation for at least a set minimum period of time is made after the first set maximum period of time has passed during which re-circulation mode operation has existed. In case of smoking activity inside the cabin, the recorded pollution level will not significantly decrease during re-circulation mode operation and, when this is recorded during a set period of re-circulation time, this triggers a switch back to inlet mode operation for at least a set minimum period of time at a preferably higher ventilation speed in order to remove the smoke from the cabin. It should be noted that tobacco smoking inside the cabin will generally lead to a much higher level of UFP pollution than the UFP pollution level existing outside the vehicle. A recorded smoking activity can be relayed as a warning message to the air pollution indicator unit 24 together will the actually recorded particle pollution level to which the vehicle inhabitants are exposed and the relative danger to human health of that recorded particle pollution level.

Also this embodiment is effective with regard to safeguarding human health for exposure to particulate pollutants, but the effectiveness remains limited and is at its best when no smoking activity occurs and when the windows are closed. Smoking activity can be more readily detected than in the embodiment of FIG. 1, but still can only unambiguously be recorded during re-circulation mode operation under conditions wherein knowledge about the presence of open windows is obtained from other electronic sensing means.

Figure 3:
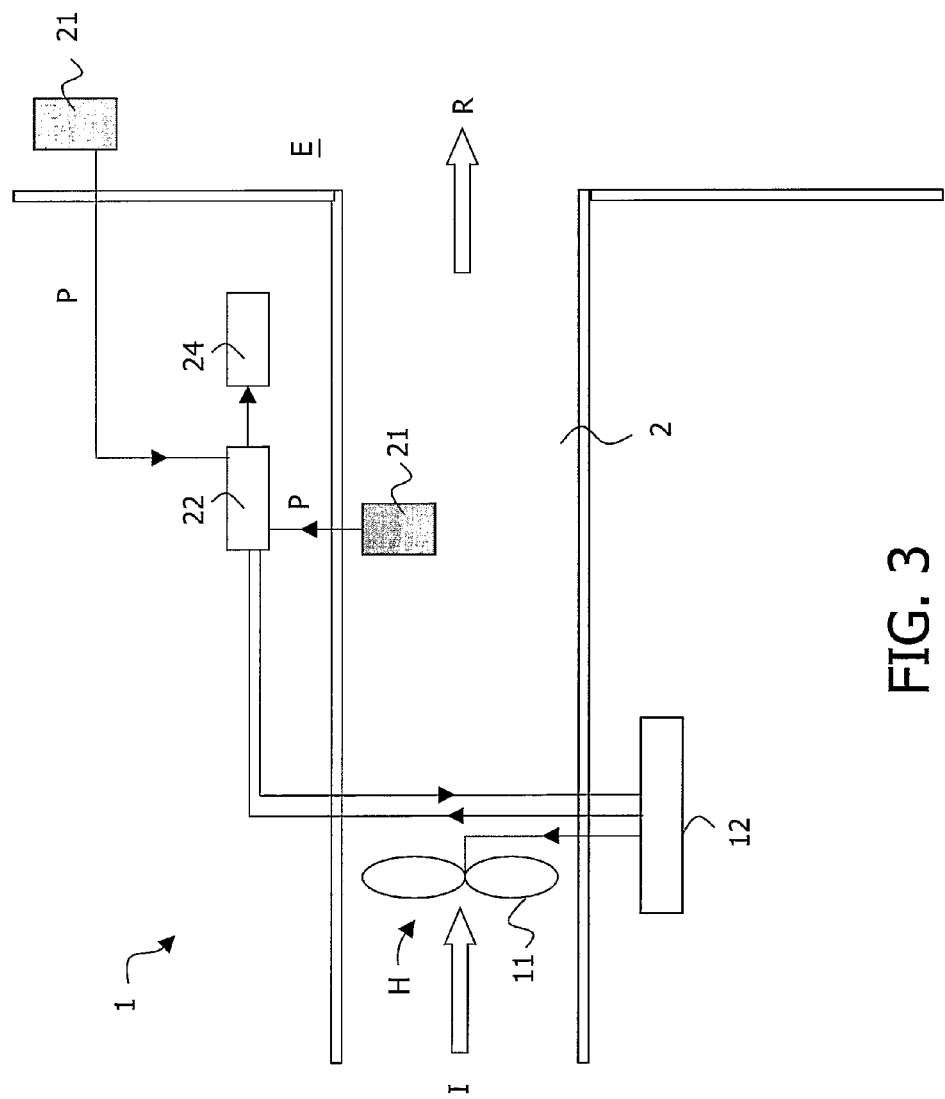

FIG. 3 shows a more preferred embodiment with particle sensors 21 in both the air duct 2 and in the cabin E. The electronic output pollution information signal P from both sensors 21 is send to an air pollution evaluation/comparator unit 22 wherein both signals are compared with each other and from where appropriate electronic feedback signals may be send to the HVAC controller unit 12 and electronic information signals to the air pollution indicator unit 24. In case no smoking occurs, both sensors 21 readings are substantially the same in any mode of HVAC operation and are independent of whether the cabin windows are open of closed. However, whether windows are open or closed can affect the recorded air pollution levels during re-circulation mode operation. Also here, a presence of open windows is best sensed by independent electronic means and relayed as a warning message to the vehicle inhabitants. During normal inlet mode operation, a smoking activity will betray itself through a measurement by the sensor 21 in the cabin E that is substantially higher than the measurement by the sensor 21 in the air duct 2. This can be relayed as a warning to the air pollution indicator unit 24. Normal inlet mode operation may be maintained as long as the cabin sensor 21 reading is higher than the sensor reading within the air duct 2, irrespective of the actually recorded outdoor particle pollution level by the sensor 21 within the air duct 2. A switch to re-circulation mode operation will only occur when no smoking activity occurs (both readings of sensors 21 are the same) and when the recorded pollution level by the sensor 21 in the air duct 2 exceeds a certain set pollution level. Re-circulation then proceeds for at the most a set maximum period of time or until the reading of the sensor 21 has dropped below a set pollution level after which normal inlet mode operation is again chosen for at least a set minimum period of time. It is noted that also re-circulation mode operation may still allow for the introduction of a (very) limited amount of outside air into the vehicle cabin via the duct 2.

The embodiment of FIG. 3 provides an improved embodiment to protect human health primarily because of its extended sensing capability as compared to the embodiments shown in FIGS. 1 and 2 with respect to smoking activities.

Figure 4:
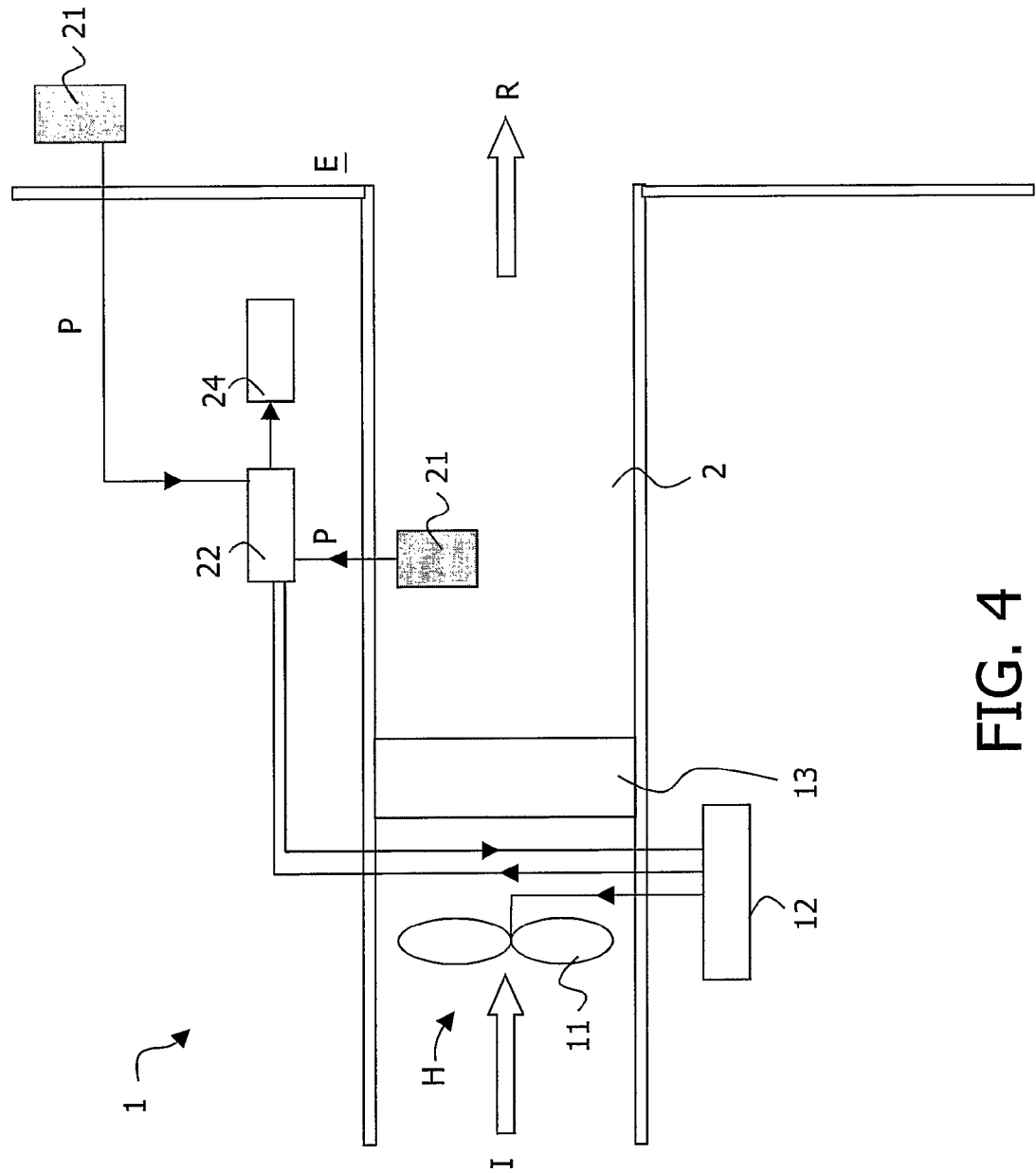

The embodiment shown in FIG. 4 is similar to those shown in FIGS. 1-3, respectively, apart from a passive air cleaning unit 13. The air cleaning unit may comprise e.g. a fibrous (electret) filter and possible additional filtration means for the removal of polluting gases from the air. The presence of the air cleaning unit 13 allows a quicker reduction of the particle pollution level during re-circulation mode operation described with reference to FIGS. 1-3.

Figure 5:
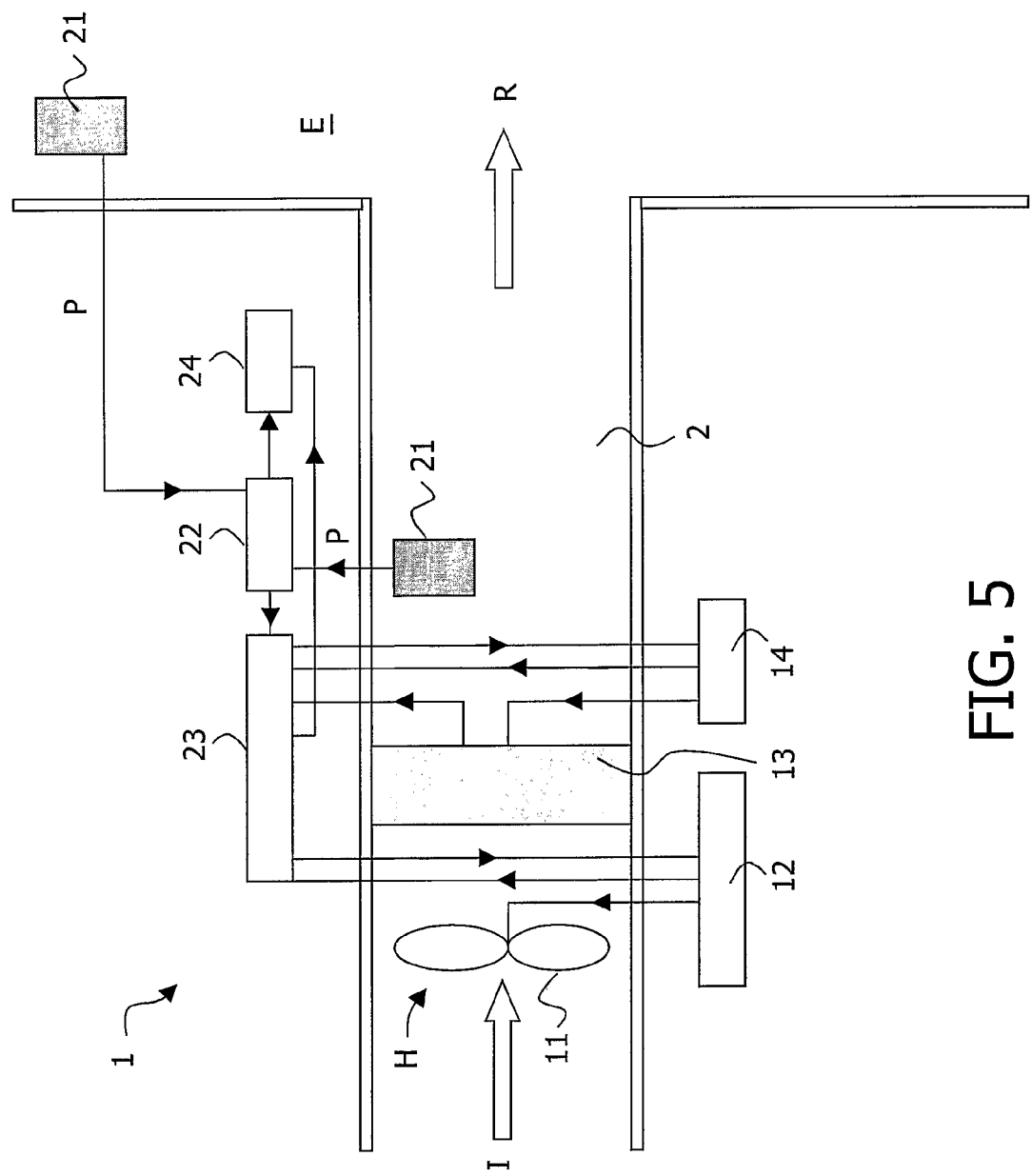

The embodiment of the invention shown in FIG. 5 is a more preferred embodiment because also an air cleaning unit 13 comprising an electrostatically augmented particle filter together with a particle charging section is provided, which will be described hereinafter in more detail. Electrostatically-augmented particle filters have the general characteristic that their particle filtration efficiency is augmented through the presence of a deliberately applied electric field within the filtration regions where the actual particle removal from air occurs. This deliberately applied electric field may also lead to field-induced leakage currents inside the filter and, in order to at least partly counteract such leakage currents, it is common practice to avoid the presence of conducting materials at locations wherein (physical) connections must be made between materials that are have different electric potentials with respect to each other. Electronic feedback signals may be relayed from the air pollution evaluation unit 22 to the air cleaning controller 14 and it may be sensed whether the end of filter lifetime has been reached by e.g. recording the overall leakage current occurring inside the electrostatically augmented particle filter while taking account of the relative humidity of the air passing through the air cleaning unit. Also end-of-filter lifetime information can be relayed as a message to the vehicle inhabitants. Air cleaning occurs to a significant extent inside the air cleaning unit 13 and normal inlet mode operation can be maintained for most of time thus allowing a more healthy air quality.

Figure 6:
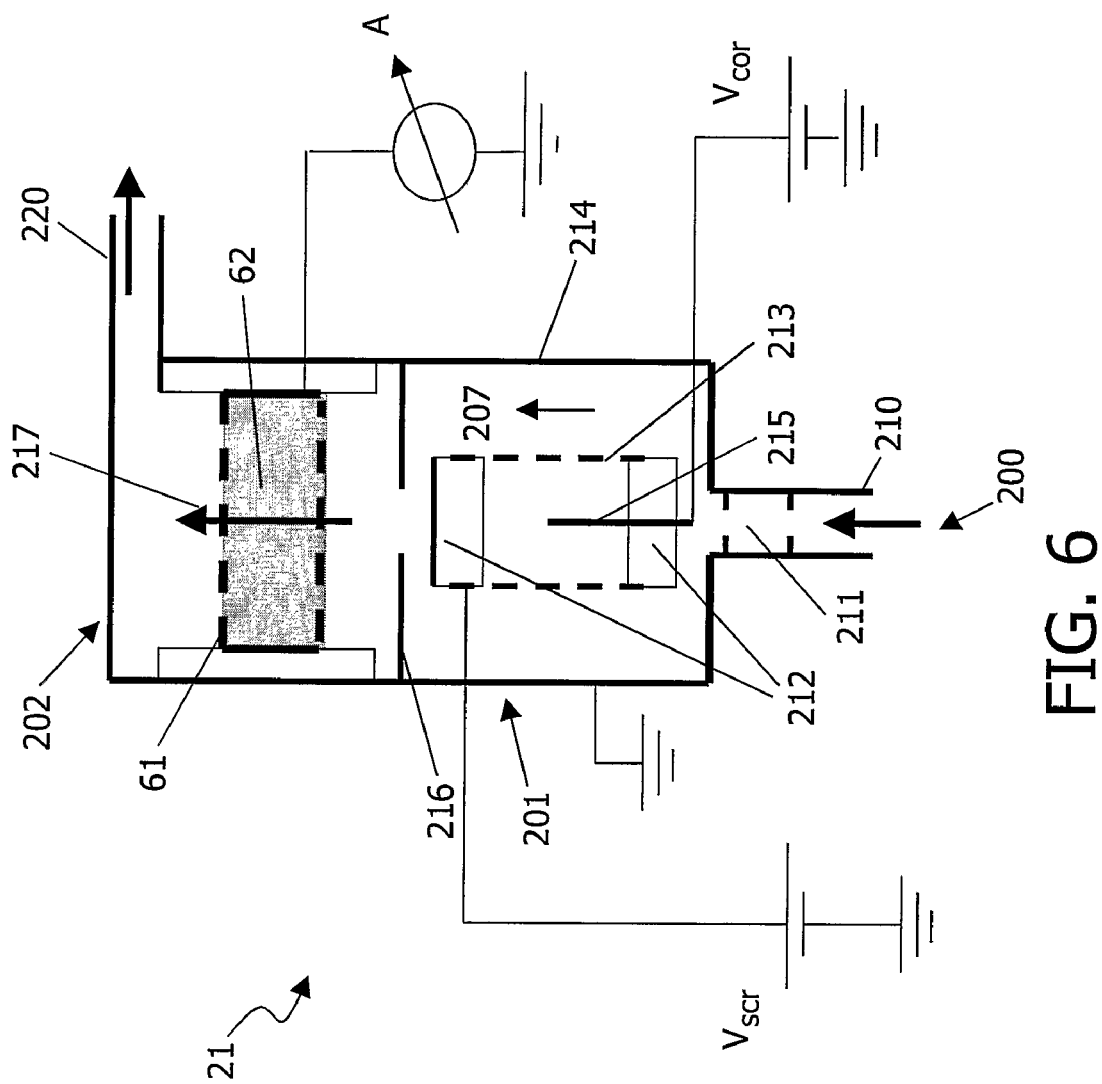
FIGS. 6-9 show schematic illustrations of UFP sensor units, according to embodiments of the invention.
Figure 7:
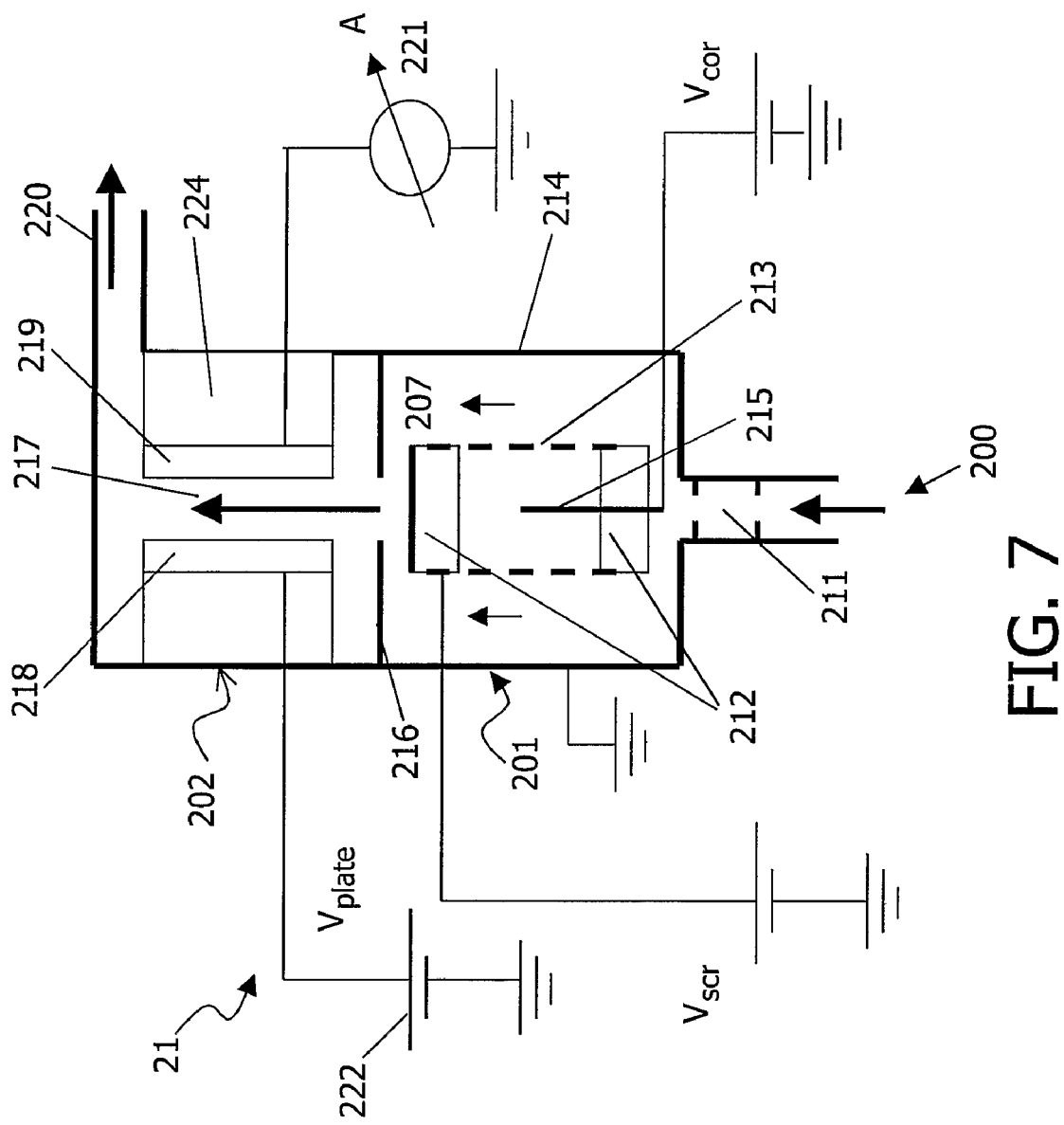

FIGS. 6 and 7 show schematic illustrations of UFP sensor units 21, according to embodiments of the invention.

The UFP sensor 21 comprises an inlet section 200, which is optionally provided with a particle pre-filter 211 serving to remove relatively large airborne particles possessing a diameter larger than about 1 μm from said input influx airflow passing through said inlet section, a charging section 201, which comprises a source of unipolar ions, the unipolar ions partly attaching themselves to the airborne particles in the air moving through the UFP sensor 21, thereby inducing either particle diffusion charging or particle field/diffusion charging, dependent on the electric field strength to which the particles are exposed during their electrostatic charging, and a particle precipitation section 202, wherein the charged particles are either electrostatically precipitated onto an electrode surface that is connected via a sensitive current meter to earth potential or wherein the charged particles are filtered out of the air by means of a filtration unit enclosed within a so-called electrically conducting Faraday cage that is connected via a sensitive current meter to earth potential (in each case giving rise to an electrical current with a magnitude that is proportional to the amount/concentration of airborne charged UFPs).

According to another preferred embodiment, the UFP sensor itself comprises, as described below in more detail with reference to FIGS. 8 and 9, an inlet section 200, which is optionally provided with a particle pre-filter 211 serving to remove relatively large airborne particles possessing a diameter larger than about 1 μm from said input influx airflow passing through said inlet section, and a particle precipitation section 202, wherein the charged particles are either electrostatically precipitated onto an electrode surface that is connected via a sensitive current meter 221 to earth potential or wherein the charged particles are filtered out of the air by means of a filtration unit enclosed within a so-called electrically conducting Faraday cage 161 that is connected via a sensitive current meter 221 to earth potential (in each case giving rise to an electrical current with a magnitude that is proportional to the amount/concentration of airborne charged UFPs).

The air handling system or air cleaning sub-system, also described later in more detail with reference to FIGS. 10-14, comprises a particle charging section 1001, for the electrostatic charging of airborne particles, in particular of airborne UFPs, in the airstream moved by e.g. the ventilator 11 and a filtering section 1002, for removing charged particles from air.

The particle charging section 1001 for the electrostatic charging of particles, in particular of UFPs comprises either photoelectric particle charging means, through the irradiation of the air containing the airborne particles with ultraviolet radiation of a photon energy above the photo-threshold of the particles or field/diffusion charging means, by exposing the air containing the airborne particles to a stream of positively or negatively charged small ions formed by a corona discharge from at least one thin-wire electrode or from at least one needle-tip electrode whereupon a high voltage is imposed or a combination of photoelectric charging and field/diffusion charging means.

The filtering section 1002, provided for removing at least a part of the charged particles from the airstream comprises either an electret filter embodied as a fibrous filter wherein a significant bipolar charge is permanently present on the polymeric fibres, an electrostatically-augmented filter embodied as a fibrous filter material sandwiched between two porous electrically-conducting gauzes, an electric potential difference being applied between the two gauzes to generate a strong electric field across the fibrous filter material which strongly enhances the particle filtration efficiency or a parallel-plate type of charged-particle precipitator filter embodied as a set of parallel plates that are alternately connected to earth potential and to a high-voltage, the parallel plates being positioned side-by-side with respect to each other each extending in a plane substantially parallel to the direction of the air flow. The advantage of a parallel-plate type of particle precipitator filter lies in its very low incurred pressure drop, the disadvantage being that it is relatively difficult and thus costly to manufacture, to clean, and/or to dispose of.

All of the above-mentioned particle filtration systems may be combined with an activated carbon filter and/or a photocatalytic filter and/or specific gas absorption/adsorption filters serving to clean the air, led through the vehicle's air handling system, at least partially from VOCs, $NO_x$, $SO_2$ and $O_3$.

The electronic controlling part of the air pollution sensor system, shown in FIGS. 1-5, allows for electronic feedback control to the vehicle's air handling system and the electrostatic air cleaning system contained inside the air handling system, based on the received electronic output signal from these systems (that corresponds with the settings of these systems), and on the electronic output signal from the UFP sensor and, optionally, the electronic output signals from separate humidity/temperature/carbon dioxide sensors.

It can be noted that the magnitude of the airborne UFP concentration may have a proportionality with the concentration of common exhaust gases such as $SO_2$, VOC's, CO and $NO_x$. As such, the functionality of the present invention not only incorporates the functionality of the prior art gas sensor system (which senses and responds to relative changes in the air pollution level within a given time interval) but extends thereupon because it also allows for:

a) a direct sensing of combustion-related particles, in particular the sensing of soot particles and other UFPs in both the cabin air and, by invoking the efficiency of the air cleaning unit 13 towards UFPs, in the inlet air drawn from the outside of the vehicle upstream of the air cleaning unit (UFP concentration indicator functionality), which is highly relevant for assessing the relative air pollution levels inside and outside the vehicle's cabin and for assessing and controlling the air cleaning functionality of the air cleaning unit with respect to charged particles, in particular charged UFPs, and for adjusting the settings of the vehicle's air handling system and air cleaning unit such as to minimize the exposure of the vehicle inhabitants to air pollutants while maintaining comfortable and safe conditions inside the vehicle's cabin in terms of temperature, humidity, oxygen, and carbon dioxide levels in the cabin air;

b) the removal of soot particles and other UFPs from inlet air (taken from the outside of the vehicle) and re-circulating cabin air (air cleaning functionality). Alternatively, the proposed inventive air pollution sensor system may be incorporated in the vehicle's air handling system in addition to the prior art gas sensor system for the purpose of enabling an independent sensing of both UFPs and various gaseous pollutants in the inlet air and in the cabin air of the vehicle in addition to providing feedback control to the operation and settings of the vehicle's air handling system and to check upon and control the air cleaning functionality of the air cleaning unit inside the air handling system.

The design rules of UFP sensors for general-purpose UFP measurements in air are partly known from prior art (see DE 198 24 744 A1), which may be considered as incorporated to the present patent application as a known document). It is advantageous to specifically tailor these design rules for the present application.

More precisely, in the present implementation of the invention, for UFP sensing in an vehicle cabin E, a UFP sensing device such as depicted in FIG. 6 is advantageously used. As previously mentioned, said device includes an inlet section 200, a charging section 201, and a particle precipitation section 202.

The inlet section 200 preferably comprises an inlet port 210, intended to receive a cold influx airflow with charged and uncharged particles, the inlet port preferably comprising a coarse particle pre-filter 211 for capturing relatively large particles from the influx airflow. The pre-filter 211 enables the mechanical removal of at least part of the large airborne dust particles, possessing a diameter larger than approximately 1 μm, from the influx airflow before being able to enter the charging section, thereby prohibiting a quick soiling of the interior of the UFP sensing device by particle deposits (said large airborne dust particles usually comprise most of the airborne particle mass). Soot particles and other UFPs are generally smaller than said large airborne dust particles and are therefore not substantially removed from the air entering the charging section by said coarse particle pre-filter.

The charging section 201 receives the influx airflow from the inlet section 200 and serves to impart an electrostatic charge onto the airborne particles in the received influx airflow from the inlet section 200 by exposing them to unipolar airborne ions under conditions of either diffusion charging (the particles are exposed to an electrostatic field strength below 500 V/cm) or field/diffusion charging (the particles are exposed to an electrostatic field strength above 500 V/cm). Under conditions of diffusion charging, the charging section comprises an ion source, a porous screen electrode 213, a counter-electrode, and a first flow conduit 207 for the influx airflow received from the inlet section 200 that is located between the porous screen electrode 213 and the counter electrode. The ion source produces airborne ions and is preferably embodied either as a needle-tip electrode or as a thin-wire electrode (not shown; this electrode is then held in position between two insulators 212) whereupon a corona voltage $V_{cor}$ is imposed that is sufficiently high to ionize the air in the direct neighborhood of the needle-tip or a thin-wire, respectively. The porous screen electrode 213 is positioned around said ion source 215 and is set at a voltage $V_{scr}$ that is substantially smaller than $V_{cor}$ causing ions of one polarity to be drawn from the ion source 215 towards the screen electrode 213. The counter-electrode is positioned around the porous screen electrode 213 and is set at a counter-electrode potential that is smaller than $V_{scr}$, the counter-electrode potential preferably being set to earth potential. This enables part of the unipolar ions drawn from the ion source 215 towards the porous screen electrode 213 to traverse the pores of the screen electrode 213 and to become drawn across the first flow conduit 207 towards the counter electrode under the driving force of the electric field existing between the porous screen electrode and the counter electrode, the electric field having a strength that is preferably kept below 500 V/cm. Part of the unipolar ions that are drawn across the first flow conduit 207 will attach themselves to the airborne particles present in the received influx airflow, thereby inducing a diffusion charging of these airborne particles. The inner wall of the housing 214 of the UFP sensor facing the screen electrode may be utilized as the counter electrode.

Under conditions of field/diffusion charging, the charging section comprises an ion source, a counter electrode, and a first flow conduit for the influx airflow received from the inlet section that is located between the ion source and the counter electrode. The ion source produces airborne ions and is preferably embodied either as a needle-tip electrode or as a thin-wire electrode held in position between two insulators. A sufficiently high corona voltage $V_{cor}$ is imposed on the needle-tip electrode or the thin-wire electrode to ionize the air in the direct neighborhood of the needle tip or the thin wire, respectively. The difference between $V_{cor}$ and the voltage imposed on the counter-electrode (preferably earth potential) induces an electric field across the first flow conduit that draws unipolar ions directly from the ion source across the first flow conduit towards the counter-electrode, thereby allowing part of the unipolar ions to attach themselves to the airborne particles in the influx airflow that moves through the first flow conduit, thus enabling a particle field/diffusion charging to be accomplished in the presence of the electric field across the first flow conduit that will generally have a strength exceeding 500 V/cm. The inner wall of the housing of the UFP sensor facing the ion source may be utilized as the counter electrode.

The particle precipitation section 202 comprises a second flow conduit 217 which is either present (FIG. 7) between two parallel electrode surfaces 218 and 219 (between which a high voltage supply 222 connected to the inner electrode 218 creates a high electric field that causes substantially all charged particles to deposit on the electrode 219 that is connected via a sensitive current meter 221 to earth potential) or which passes (FIG. 6) through a fibrous dust filter 62 located within a so-called Faraday cage 61 causing charged particles to deposit on the fibers of the dust filter inside the Faraday cage, the Faraday cage being connected via a sensitive current meter to earth potential. In all cases, the deposited charge per unit time inside the precipitation section 202 is measured as an electric current I through the said current meter. At least in case of diffusion charging (but also in case of field/diffusion charging when the encountered UFP pollution level is mostly derived from particles with a diameter $d_p$<300 nm), where the acquired particle charge is approximately proportional to the particle diameter $d_p$, the measured current I becomes approximately proportional to the total length concentration $L_{ufp}$ of all airborne UFPs. Thus, $$I \propto L_{ufp} = \int_{dp=0}^{dp=500\,nm} d_p \frac{dN_{ufp}}{d\ln d_p} d\ln d_p$$

wherein $dN_{ufp}/d\ln(d_p)$ represents the particle number concentration as a function of the particle size (i.e. the particle size distribution). Since $L_{ufp}$ is approximately proportional to the UFP-associated human health impact parameter $H_{ufp}$, given by $$H_{ufp} \approx Const_1 \int_{dp=10\,nm}^{dp=500\,nm} d_p^{1.5} \frac{dN_{ufp}}{d\ln(d_p)} d\ln(d_p)$$

with $Const_1$ a constant parameter depending on the physical composition of the particles, it follows that to a reasonable approximation, $H_{ufp} \propto I$ The magnitude of the measured current I is thus approximately proportional to the relative health-hazardousness of the encountered UFP pollution concentration, which is most relevant for the present application. The $d_p^{1.5}$ dependency in the expression for $H_{ufp}$ is obtained from a multiplication of the relative health hazard of deposited particles within the alveolar region of the lungs (proportional to their surface area ($\sim d_p^2$)) with the deposition efficiency of these particles inside the alveolar region of the lungs (approximately proportional with $d_p^{-0.5}$). Preferably, the source of the airborne UFPs should be known (e.g. automobile traffic) in order to determine a reliable proportionality factor between I and $H_{ufp}$. Accordingly, data is obtained about the relative health impact $H_{ufp}$ of the UFP-polluted air from a recording of the current I.

With respect to the sensor housing 214, the electrodes 218 and 219 are electrically isolated by means of dielectric insulation elements 224 that possess a very high electrical resistance.

For the embodiments of the UFP sensor 21 depicted in FIGS. 6 and 7, it is advantageous to ensure that the readings of the electric current meter 221 are not affected through a presence of residual airborne unipolar ions that are electrically drawn from the charging section 201 into the precipitation section 202 or carried along with the air when the said input influx airflow passes from the charging section 201 into the precipitation section 202. For this purpose, an earthed baffle plate 216 is preferably disposed in between the charging section 201 and the precipitation section 202 in order to allow a flow conduit to be established between the said baffle plate 216 and the surface of the insulator 212 facing the said baffle plate. By imposing a small electric field strength across the said flow conduit existing between the baffle plate 216 and the top surface of the insulator 212 facing the baffle plate 216, residual unipolar ions are readily removed from the airflow entering the precipitation section 202 while hardly affecting the passage of charged UFPs because of the much smaller electrical mobility of charged UFPs with respect to the electrical mobility of unipolar ions.

The top surface of the insulator 212 facing the baffle plate 216 assumes an electric potential that is different from earth potential by covering it with an electrode plate that is connected to the potential $V_{scr}$. It is note that the plate may also be connected to the potential $V_{cor}$. Further, the insulator may be left uncovered under which condition it will readily acquire a finite electric potential through the absorption of unipolar ions from air.

Figure 8:
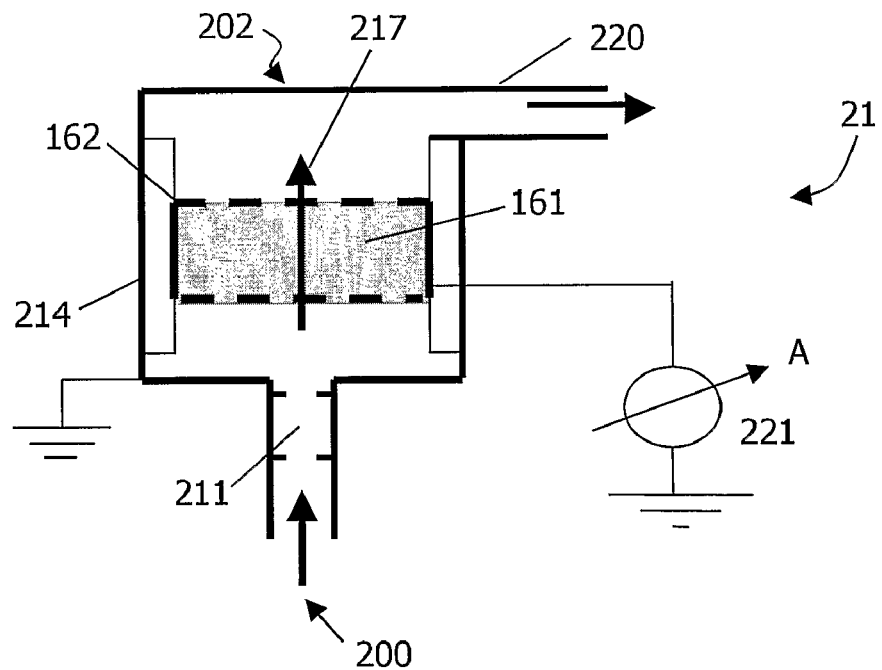
Figure 9:
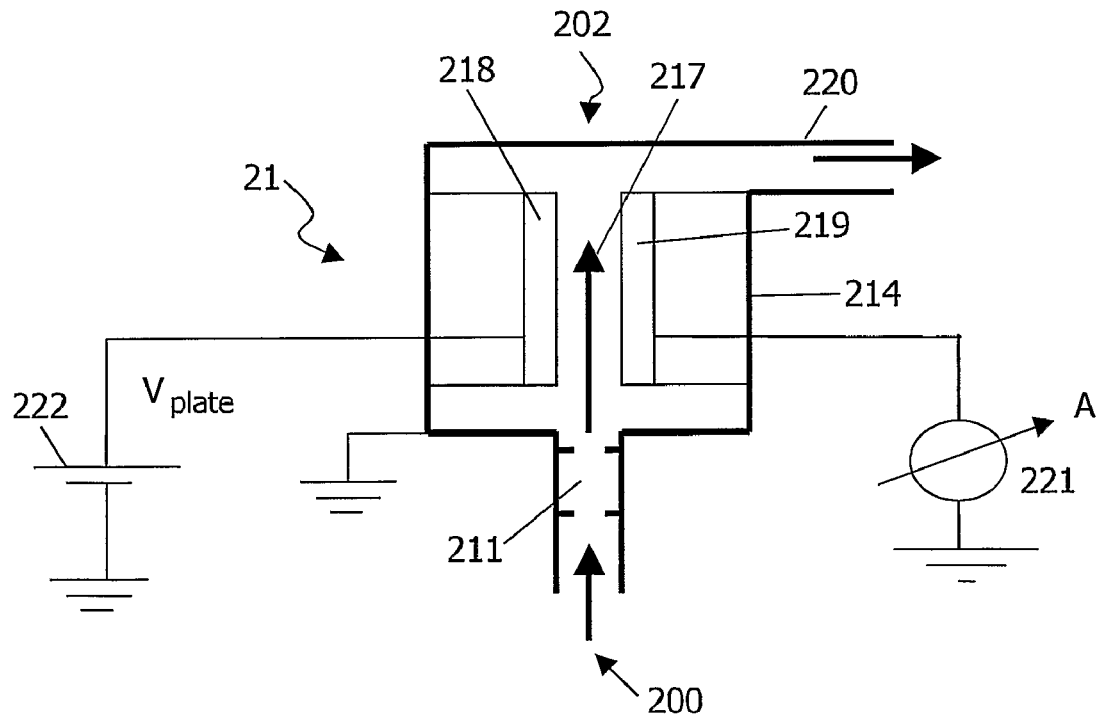

Two alternative embodiments are proposed in FIGS. 8 and 9 in which no particle charging occurs, but wherein only particle capture occurs. The UFP sensor in FIG. 8 comprises a particle precipitation section 202 consisting of a porous particle filter 161 inside a Faraday cage 162, while FIG. 9 shows an UFP sensor 21 comprising a particle precipitation section 202 consisting of two parallel electrode plates 218 and 219 between which an electric field is created by connecting a high-voltage supply 222 to the high-voltage plate 218 of the parallel-plate precipitator and connecting the electrode plate 219 via a sensitive current meter 221 to earth potential. The UFP sensor units 21 in FIGS. 8 and 9 both comprise an air inlet 200 that is optionally provided with a coarse particle pre-filter 211, and an air exit 220 connected to a pump or fan that draws air through the said UFP sensor units. The UFP sensor units 21 in FIGS. 8 and 9 only sense the presence of charged airborne particles that have escaped capture in the filtering section of the air cleaning unit 13 upstream of the said UFP sensors, the particle charging then being accomplished by the particle charging section 1001 of the air cleaning unit 13 (see FIG. 10 ff). Particle sensing in the said UFP sensors 21 occurs by recording the current through the current meter 221 that results when charged particles precipitate either inside the porous particle filter 161 (in FIG. 8) or on the earthed electrode plate 219 (in FIG. 9). When the particle charging in the particle charging section 1001 occurs through photo-electric charging, the UFP sensors in FIGS. 8 and 9 behave as soot sensors because only soot particles can be readily charged through photo-electric charging with a UV lamp. In case the particle charging in the particle charging section 1001 occurs through corona diffusion charging or corona field/diffusion charging or through a combination of corona charging and photo-electric charging, the UFP sensors in FIGS. 8 and 9 behave as true UFP sensors because substantially all airborne particles become charged.

The airflow through said UFP sensors 21 in FIGS. 6-10 will normally be limited to no more than a few liters/minute and can be established by a ventilator or pump (not shown) connected to an air exit 220 receiving said output airflow delivered by said precipitation section.

It should be noted that the total airflow through the integrated air cleaning unit 13 (FIG. 5) located upstream of the UFP sensor can amount up to 10 m³/min in case the air handling system of an ordinary passenger car is involved, and is thus many orders of magnitude higher than the airflow through the UFP sensor unit 21.

The integrated air pollution sensor system 1 is preferably situated in the vehicle's air handling system at a location where the temperature of the air passing through the air handling system has been adjusted such as to come close to room temperature conditions. This is preferably accomplished by positioning the integrated air cleaning/sensor/controller system downstream of the cooling heat exchanger and/or heating heat exchanger components associated with the vehicle's air handling system, thereby ensuring the operation of the UFP sensor 21 to be rather independent of the outside air temperature and the relative humidity in the outside air.

Figure 10:
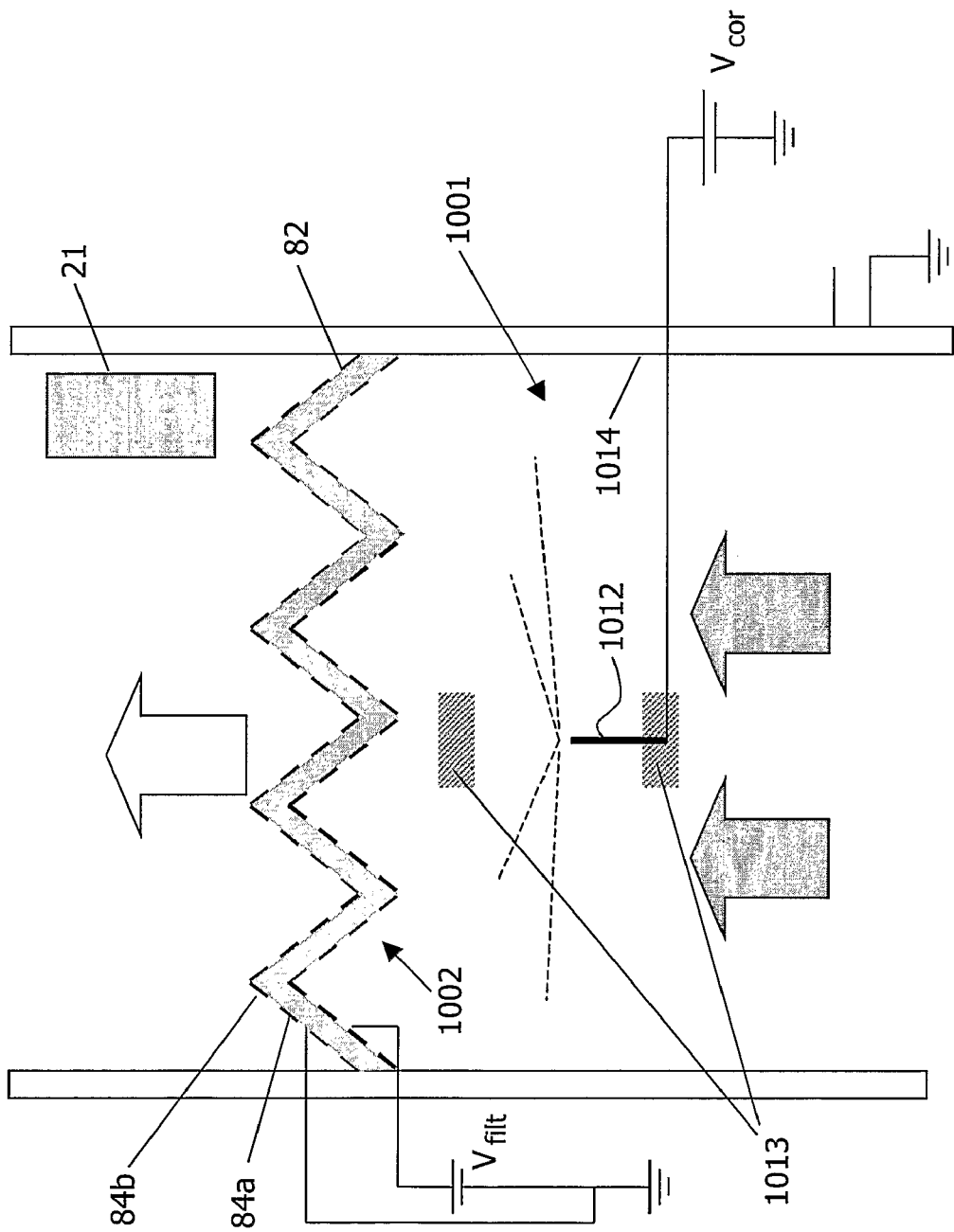
FIGS. 10-14 show schematic illustrations of air handling systems, in particular air cleaning units, according to embodiments of the invention.

One embodiment for an UFP pollution sensor system 1 comprising air cleaning system for removing UFPs from the air moved by the vehicle's air handling system is shown in FIG. 10, in which the particle charging section 1001 comprises a source of unipolar ions embodied as a needle-tip corona-discharge electrode 1012 located upstream of the filtering section 1002, which is, in the present case, an electrostatically-augmented fibrous filter 82. The needle-tip electrode 1012 is set at a sufficiently high voltage $V_{cor}$ to induce a corona discharge from the needle-tip, thereby sending a stream of unipolar ions away from the needle-tip electrode towards a counter-electrode set at a lower potential, the counter-electrode being formed, at least in FIG. 10, by the earthed inner wall 1014 of the duct through which the air is moved by the vehicle's air handling system. In particular when the needle-tip electrode 1012 is located in close proximity to the electrostatically-augmented filter 82 (or any other type of particle filter), it is advantageous to position a dielectric insulator element 1013 inside the space existing between said needle-tip electrode and the fibrous particle filter, this insulator blocking the sight of at least part of the face of the electrostatically-augmented filter when viewed from the position of the needle-tip electrode but positioned sufficiently far from said needle-tip electrode to ensure the corona discharge from the needle-tip electrode to remain substantially undisturbed by the presence of said insulator. When unipolar ions are emitted from the needle-tip electrode 1012, some of these unipolar ions quickly adsorb onto and thus charge said insulator 1013, thereby raising the electric potential of said insulator which avoids or at least diminishes a direct passage of emitted unipolar ions from the needle-tip electrode towards the side of the particle filter facing said needle-tip electrode, thus ensuring that the trajectories of the emitted unipolar ions are substantially directed from the needle-tip electrode towards the earthed inner wall 1014 of the duct serving as a counterelectrode. The trajectories of the emitted unipolar ions towards the inner wall 1014 of the duct cross the trajectories of the airborne particles moving along with the airflow and allow for ion attachment to the airborne particles, thereby enabling particle field/diffusion charging during the residence time of the particles in the particle charging section. The magnitude of the particle charge is a function of the residence time of the particles in the particle charging section, the particle size, and the electric field strength exerted onto the particles during their charging.

It should be noted that needle-tip electrode 1012 of FIG. 10 may be replaced by a thin-wire electrode located between dielectric insulators (not shown). The air in the direct vicinity of the thin-wire electrode becomes ionised when a sufficiently high voltage $V_{cor}$ is imposed on the thin-wire electrode.

It is noted that in practical automotive air handling units, that may be engineered to displace airvolumes of sometimes over 500 m³/hour, one will generally install several parallel-positioned high-voltage needle-tip electrodes and/or thin-wire electrodes together with several counter electrodes inside the particle charging section according to one of a number of possible design options that are well known to those skilled in the art.

Figure 13:
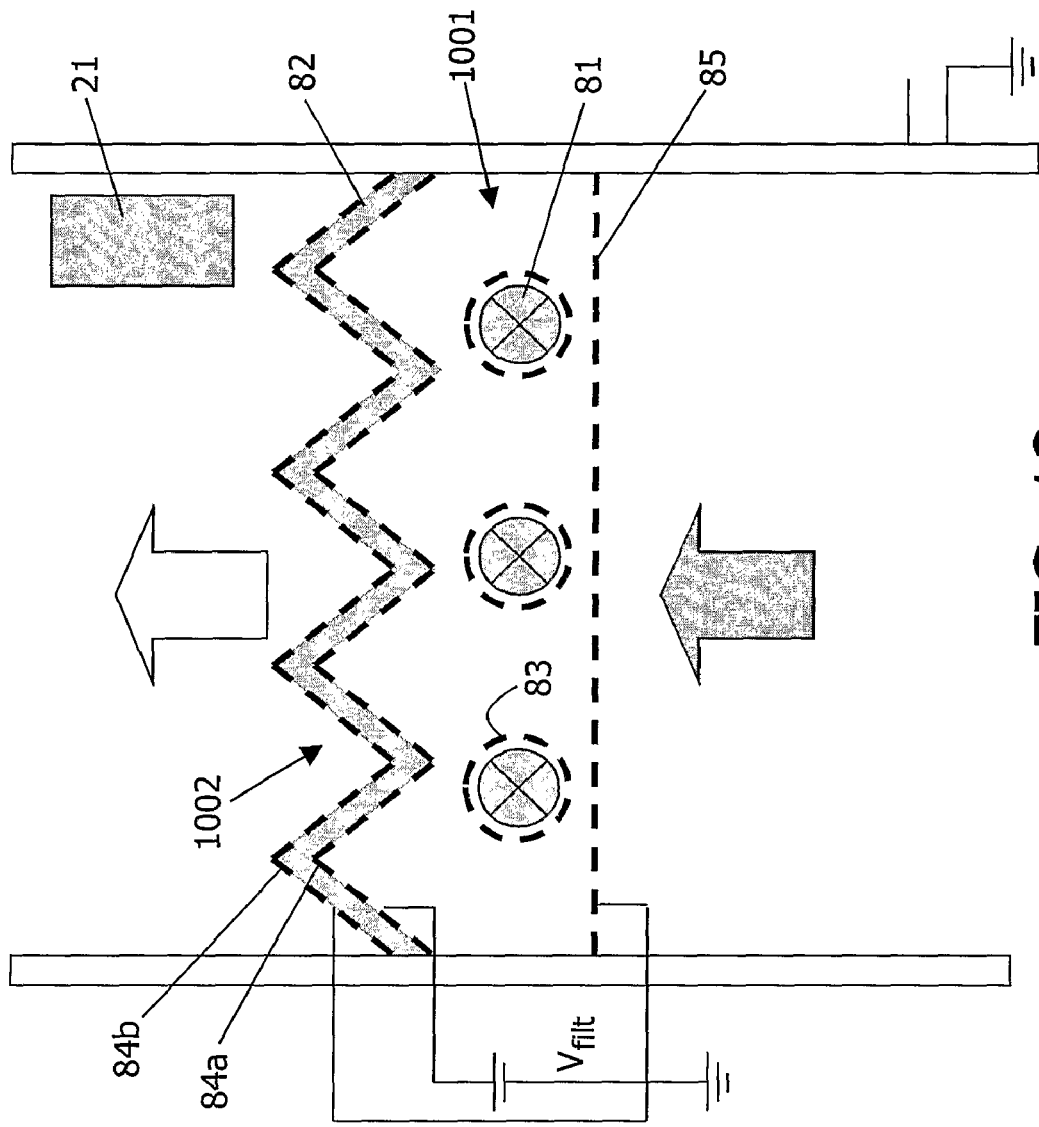

In another embodiment of the particle charging section 1001, shown in FIG. 13, said particle charging section 1001 comprises (extended) meandering UV light sources 81 positioned upstream of the filtering section 1002, which may be an electrostatically-augmented fibrous filter 82. These UV light sources 81 irradiate all particles present in the airflow passing though the air handling unit with UV light comprising a wavelength below 260 nm, thereby imparting a photo-electrically-induced positive charge onto the airborne UFPs, in particular onto the airborne soot particles. The magnitude of the created charge on the soot particles depends on the particle size and has a proportionality with the product of the illumination intensity of the UV light received by the particles and the residence time of the particles in the UV-illuminated region. The (meandering) tubular UV light sources 81 are shielded from direct exposure to the airflow by disposing an electrically conducting gauze 83 of high porosity around each UV source, which avoids a quick contamination of the outer surfaces of these UV light sources by depositing particles. The gauzes 83 are preferably earthed. The surfaces of the gauzes 83 are preferably covered with a thin coating of a non-metallic material, the said coating being sufficiently thick to quench the photo-emission of electrons from the said surfaces of the gauzes 83 when the said surfaces are illuminated with UV light emitted from the said UV light sources, the said coating being sufficiently thin to guarantee a finite electrical conductivity across the said coating. A quenching of the photo-emission of electrons from the surfaces of the gauzes 83 is desirable because such emitted electrons are capable of neutralizing at least some photo-charged airborne UFPs which would reduce the overall charging efficiency of UFPs during their passage through the charging section 1001 in FIGS. 16 and 17. For the same reason, also other metallic surfaces facing the said UV light sources are preferably covered with a thin coating of a non-metallic material to prevent the photo-emission of electrons when said other metallic surfaces are exposed to irradiation with UV light.

Figure 14:
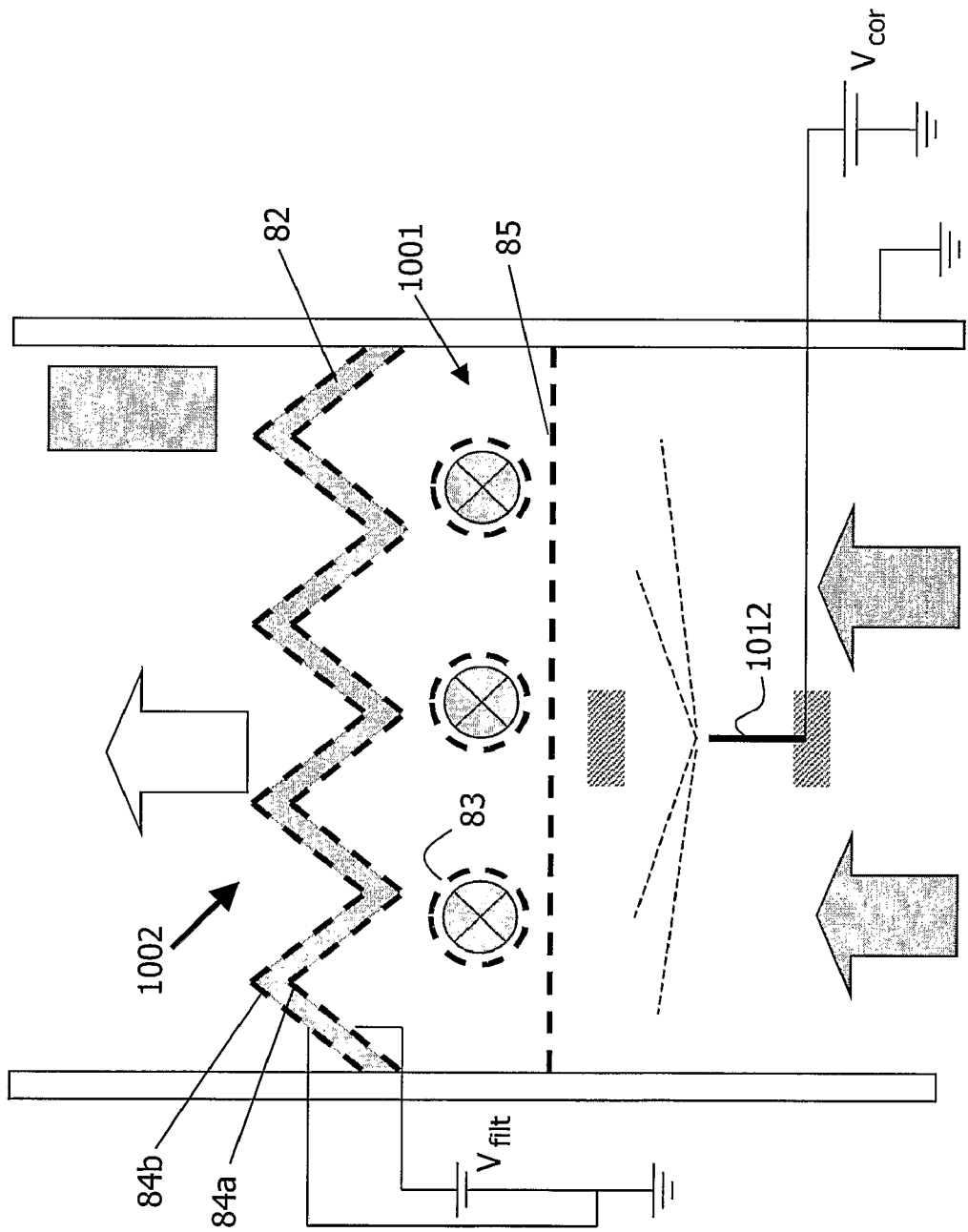

In a further embodiment, depicted in FIG. 14, field/diffusion charging of all particles occurs by means of a corona discharge from a needle-tip electrode 1012, together with photoelectric particle charging by means of UV-light sources 81, surrounded, as above, by earthed gauzes 83. Preferably, the corona discharge in this embodiment is made to emit positive unipolar ions so that the acquired positive field/diffusion charge on at least some of the UFPs, notably the soot particles, is further augmented by a positive photo-electric charge.

The electrostatically-augmented filter 82 is embodied as a pleated fibrous filter sandwiched between two porous metal gauze electrodes (84a, 84b) between which a voltage difference $V_{filt}$ is established. The resulting electrostatic field across the thickness of this fibrous filter 82 is now an externally-applied electric field which much enhances the filtration efficiency of the filter towards charged airborne particles while the incurred pressure drop across this filter can be maintained at a relatively low level. The electrostatically-augmented filter 82 removes the charged particles from air with an efficiency that increases with increasing particle charge, increasing electric field strength across the filter, and decreasing air speed through the filter. Activated carbon is preferably present either inside the electrostatically-augmented filter 82, or on the surface of the porous metal gauze electrodes (84a, 84b), or in a separate activated carbon filter downstream of the needle-tip electrode 1012, the activated carbon filter being then preferably embodied as a corrugated filter featuring substantially straight flow channels for the moving air (not shown), in order to minimize the incurred pressure drop across the activated carbon filter, and wherein the internal walls of said flow channels comprise activated carbon material. Activated carbon material can be present inside the electrostatically-augmented fibrous filter 82, for example as an activated carbon coating on the surface of at least some of the fibers from which the fibrous filter is composed. The purpose of the activated carbon is to clean the air from the ozone gas that is either produced by the corona discharge from the needle-tip electrode or thin-wire electrode 1012 and/or produced by the UV light sources 81 in the particle charging section 1001. The high-voltage gauze 84a associated with the electrostatically-augmented filter 82 preferably faces the UV light sources 81 upstream of said filter, the electrically-conducting gauze electrode 84b facing away from said charging section then being connected to earth potential. An electric field is thus created between the electrostatically-augmented filter 82 and the earthed gauzes 83 surrounding the UV light sources 81 as well as between the electrostatically-augmented filter 82 and a second earthed gauze 85 of high porosity located upstream of the UV light sources 81. This electric field enhances the photoelectric charging of particles since it enables a quick removal of photo-emitted electrons and negative small ions from air. Preferably, the high-voltage gauze 84a is connected to a high-voltage $V_{filt}$ that is positive with respect to earth potential. This has the advantage that the positively-charged particles will preferably deposit on the upstream side of the surface of the electric field-polarized fibers inside the fibrous filter which augments the particle removal efficiency from air. The gauze 84b is connected to a lower potential, preferably earth potential.

The gauze electrodes 84a, 84b do not necessarily have to be pleated in accordance with the pleating of the fibrous filter. Instead, they may also be embodied as straight non-pleated electrode gauzes that contact the fibrous filter only at the tip of the filter pleats. The spacing between the gauze electrodes will then substantially correspond with the thickness of the filter cassette wherein the pleated filter is disposed.

In yet another embodiment, the filtration section may be embodied as a non-pleated fibrous filter slab sandwiched between straight electrode gauzes. The UFP sensor 21 is located downstream of the electrostatically-augmented filter 82 and therefore senses only those particles that have been transmitted through said electrostatically-augmented filter.

Figure 12:
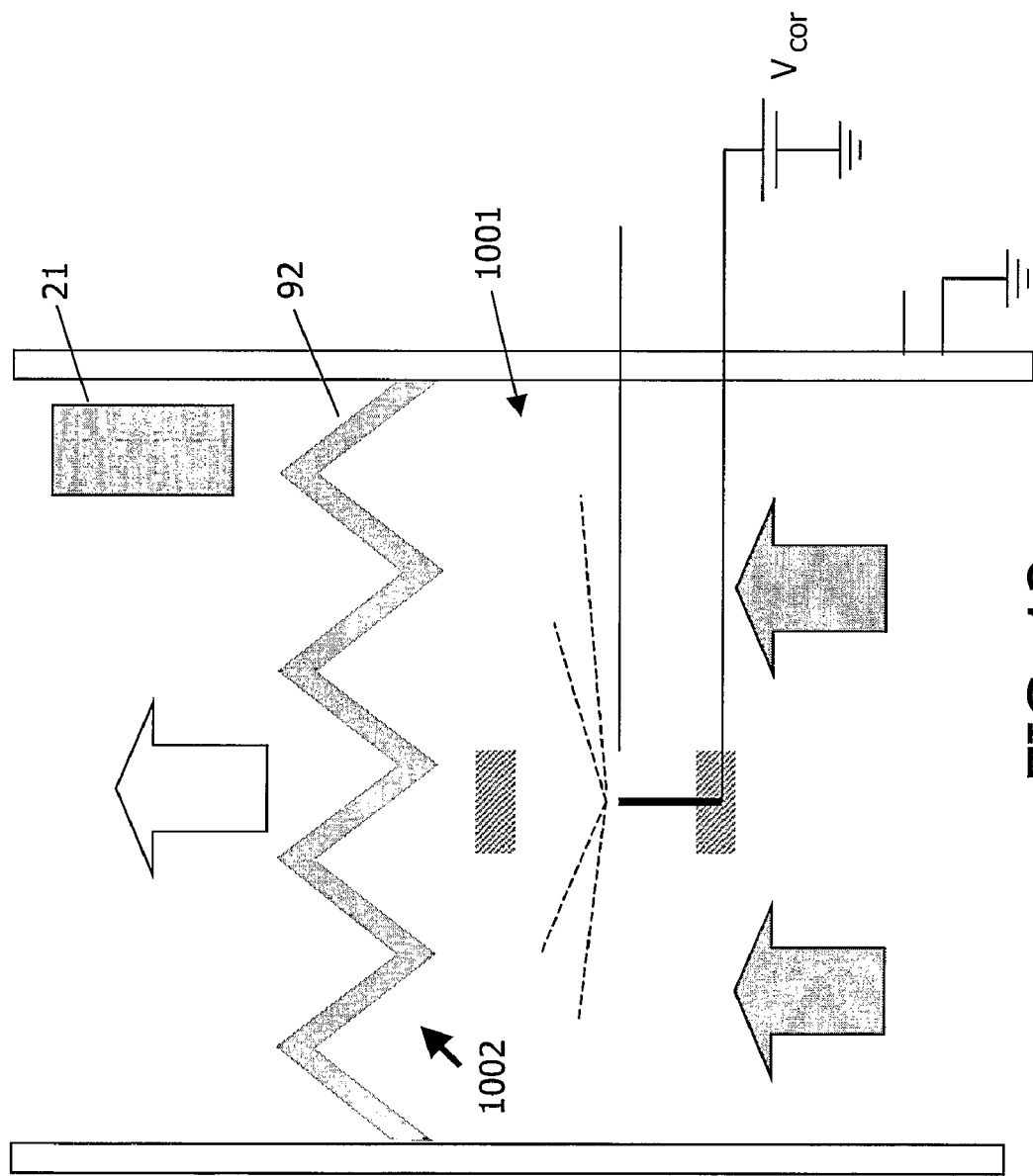

In another embodiment, depicted in FIG. 12, a fibrous electret filter 92 is used for the capture of charged UFPs and other charged particles, instead of the electrostatically-augmented one shown in FIGS. 10, 13 and 14. In this embodiment, the electret filter 92 is not sandwiched between two conductive porous gauze electrodes. An externally-applied electric field can therefore not be applied. Instead, localized electric fields exist inside the electret filter that are set up by the bipolar charge distribution on the fibers of the electret filter.

Figure 11:
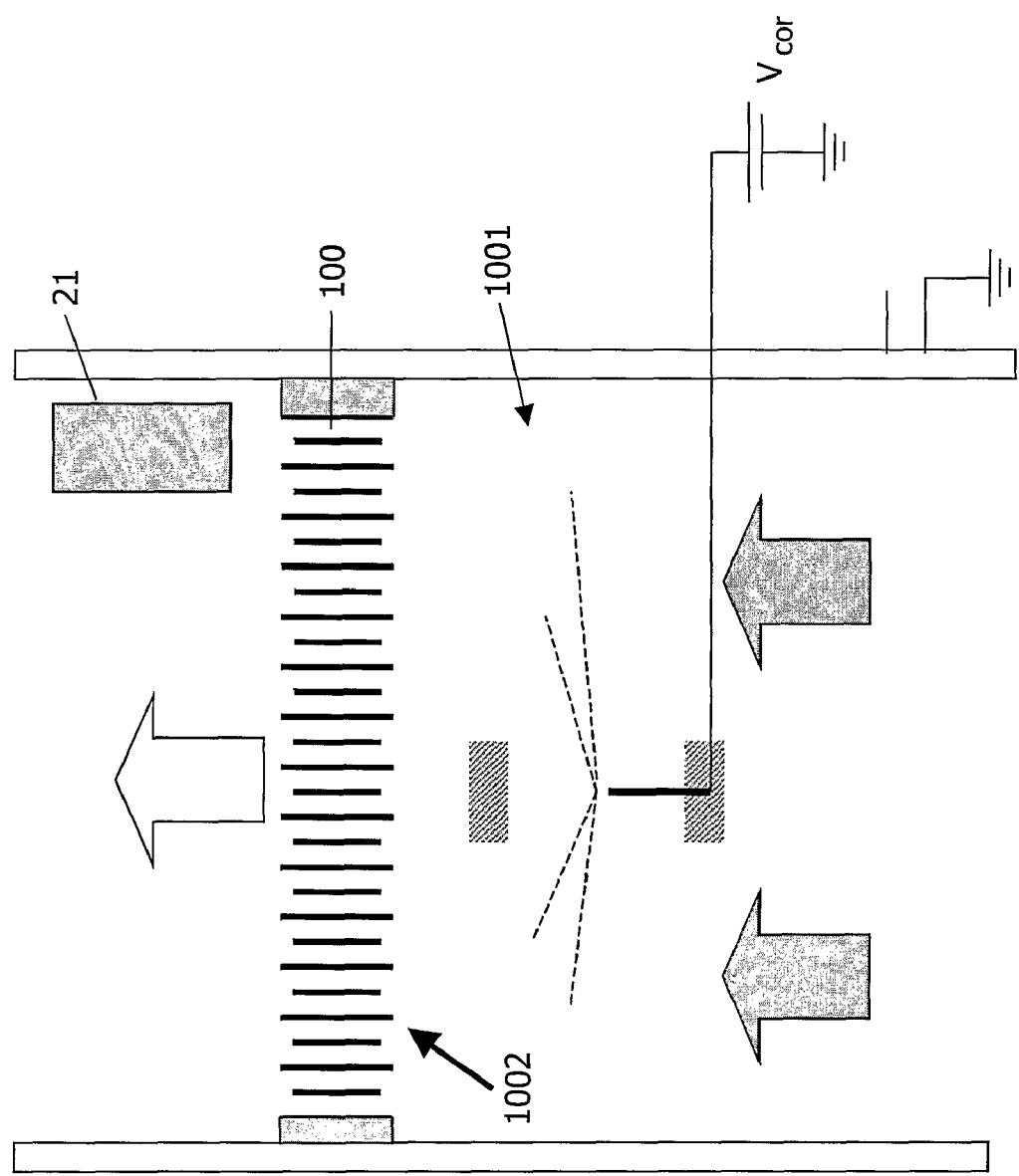

In still another embodiment, depicted in FIG. 11, the filter is a particle precipitation filter 100 comprising a set of stacked parallel plates or gauzes. Between these plates, connected alternately to earth potential (plates 101_a to 101_{n+1}) and to a high voltage $V_{filt}$ (plates 101_b to 101_n), electrostatic fields are set up that promote the deposition of charged airborne particles onto the plate surfaces.

It is advantageous to install an additional coarse fibrous particle/dust prefilter upstream of the particle charging section in the air cleaning unit 13 for the purpose of mechanically capturing coarse airborne particles, possessing a diameter larger than a few μm's, from the airflow displaced by the air handling system. This measure much extends the lifetime of the downstream electrostatically-augmented particle filter 82, electret filter 92, or parallel-plate precipitation filter 100 in the air cleaning unit 13, prevents an early fouling of the various components present inside the particle charging section, and avoids a quick increase of the pressure drop across the electrostatically-augmented particle filter 82 or electret filter 92 in the course of time due to dust deposits, while the coarse fibrous prefilter itself only incurs a very small pressure drop.

It should be noted that the above-mentioned embodiments illustrate, rather than limit, the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The mere fact that certain measures are recited in mutually different dependent claims does not indicate that a combination of these measures cannot be used to advantage.

The invention claimed is:

1. An air pollution sensor system (1) incorporated in an enclosure (E), said enclosure comprising:
   an air handling system inside an air duct (2), said air duct enabling a communication between air inside said enclosure and air outside said enclosure, said air duct comprising an air inlet for receiving air and an air outlet for releasing handled air inside said enclosure, wherein said air pollution sensor system further comprises;
   at least one particle sensor (21) for:
      sensing particles with a diameter in a range of approximately 5-2500 nm, inside said enclosure, said particle sensor comprising:
      (a) an inlet section (200) capable of receiving an input influx airflow with charged and uncharged airborne UFPs, and
      (b) a precipitation section (202; 301) capable of receiving said charged and uncharged airborne UFPs and performing an electrostatic particle precipitation or particle filtration step to capture at least part of said charged airborne UFPs and delivering an output airflow that is at least partially denuded of said charged airborne UFPs, wherein said precipitation section (202) comprises a second flow conduit (217) present between at least two cylindrical-concentric and/or parallel-plate electrodes (218,219) capable of applying a high electric field across said second flow conduit, one of these two electrodes being connected via a current meter (221) to earth potential; and
      providing a pollution information signal (P) in response to the sensing of said particles.

2. The air pollution sensor system (1) according to claim 1, wherein said air handling system further comprises:
   an air cleaning unit (13) within said air duct (2), wherein said particle sensor (21) is arranged to sense said particles downstream of said air cleaning unit.

3. The air pollution sensor system (1) according to claim 1, wherein said particle sensor (21) is arranged within said enclosure and outside of said air duct.

4. The air pollution sensor system (1) according to claim 3, wherein said air pollution sensor system comprises at least a second particle sensor unit (21) capable of sensing said particles within said air duct or immediately downstream from the said outlet of said air duct.

5. The air pollution sensor system (1) according to claim 1, wherein said air handling system comprises an electrically controllable air cleaning unit (13), and said air pollution sensor system is capable of providing said pollution information signal (P) to said air cleaning unit for controlling said air cleaning unit.

6. The air pollution sensor system (1) according to claim 1, wherein said air handling system comprises a controllable pump or ventilator unit (11) capable of displacing air between said air inlet and said air outlet of said air duct (2) and said air pollution sensor system is capable of providing said pollution information signal (P) to said pump or ventilator unit for controlling said displacement of air.

7. The air pollution sensor system (1) according to claim 1, wherein said air handling system comprises an air cleaning unit (13) capable of at least partly removing airborne particles and wherein said particle sensor unit (21) is positioned downstream of said air cleaning unit, said air cleaning unit comprising:
  (a) a charging section (1001) capable of electrically charging at least part of said airborne particles passing through said air duct;
  (b) a filtering section (1002), positioned downstream of said charging section, capable of removing at least part of the airborne particles received from said charging section,
wherein said particle sensor (21) is arranged such that at least a small volume of the airflow received from said filtering section is received by said particle sensor.

8. A sensor unit (21) for sensing of airborne ultra fine particles (UFPs) with a diameter in a range of 5-2500 nm, said sensor unit comprising:
  (a) an inlet section (200) capable of receiving an input influx airflow with charged and uncharged airborne UFPs, and
  (b) a precipitation section (202; 301) capable of receiving said charged and uncharged airborne UFPs and performing an electrostatic particle precipitation or particle filtration step to capture at least part of said charged airborne UFPs and delivering an output airflow that is at least partially denuded of said charged airborne UFPs, wherein said precipitation section (202) comprises a second flow conduit (217) present between at least two cylindrical-concentric and/or parallel-plate electrodes (218,219) capable of applying a high electric field across said second flow conduit, one of these two electrodes being connected via a current meter (221) to earth potential.

9. The sensor unit (21) according to claim 8, further comprising a charging section (201) upstream from said precipitation section capable of receiving said input influx airflow and electrically charging at least a portion of said airborne UFPs in said input influx airflow.

10. The sensor unit (21) according to claim 8, wherein said second flow conduit (217) passes through a fibrous dust filter (62) disposed in a Faraday cage (61), said Faraday cage capable of being connected via a current meter to earth potential.

11. An air handling system installed inside an air duct (2), said air duct enabling a communication between air inside said air duct and air outside said air duct, said air duct comprising an air inlet for receiving air and an air outlet for releasing handled air inside said air duct, said system comprising:
  at least one particle sensor comprising:
    (a) an inlet section (200) capable of receiving an input influx airflow with charged and uncharged airborne UFPs, and
    (b) a precipitation section (202; 301) capable of receiving said charged and uncharged airborne UFPs and performing an electrostatic particle precipitation or particle filtration step to capture at least part of said charged airborne UFPs and delivering an output airflow that is at least partially denuded of said charged airborne UFPs, wherein said precipitation section (202) comprises a second flow conduit (217) present between at least two cylindrical-concentric and/or parallel-plate electrodes (218,219) capable of applying a high electric field across said second flow conduit, one of these two electrodes being connected via a current meter (221) to earth potential; and
    providing a pollution information signal (P) in response to the sensing of said particles; and
  an air cleaning unit (13) comprising:
    (a) a charging section (1001) capable of electrically charging at least part of said particles (UFPs);
    (b) a filtering section (1002) capable of removing at least part of said charged UFPs from the airflow thus obtained from said charging section.

12. The air handling system according to claim 11, wherein said charging section (1001) comprises one or more UV-emitting light sources (81) located upstream of said filtering section (1002), said UV-emitting light sources being capable of emitting radiation with a wavelength spectrum comprising a wavelength below 260 nm.

13. The air handling system according to claim 11, wherein said charging section (1001) comprises at least one thin-wire electrode or needle-tip electrode (1012) at high voltage capable of exposing said airflow passing through said air duct to a stream of charged unipolar ions formed by a corona discharge from said thin-wire electrode or from said needle-tip electrode.

14. The air handling system according to claim 11, wherein said filtering section (1002) comprises activated carbon capable of cleaning said airflow from ozone gas.

15. The air handling system according to claim 11, wherein said filtering section (1002) comprises an electrostatically augmented particle filter (82) located downstream of said charging section.

16. The air handling system according to claim 15, wherein said electrostatically augmented particle filter is a pleated electrically non-conductive fibrous filter sandwiched between two electrically conductive porous layers (84a,84b) between which a voltage difference can be established, thereby creating an externally-applied electric field across said electrically non-conductive fibrous filter.

17. The air handling system according to claim 16, wherein the electrically conductive porous layer facing said charging section is connected to a high voltage potential (Vfilt) and in which the electrically conductive porous electrode facing away from said charging section is connected to earth potential.

18. The air handling system according to claim 15, wherein said electrostatically augmented particle filter (82) is a fibrous electret filter.

19. The air handling system according to claim 15, wherein said electrostatically augmented particle filter is a parallel-plate type precipitation filter (100), the air handling system being arranged such that one of said parallel plates of said precipitation filter are connected to a high voltage potential (Vfilt) and another of said parallel plates are connected to earth potential.

* * * * *